US00PP22035P2

(12) United States Plant Patent
Zerr

(10) Patent No.: US PP22,035 P2
(45) Date of Patent: Jul. 19, 2011

(54) POINSETTIA PLANT NAMED 'SYEP22432'

(50) Latin Name: *Euphorbia pulcherrima*
Varietal Denomination: SYEP22432

(75) Inventor: Katharina Zerr, Höhr-Grenzhausen (DE)

(73) Assignee: Syngenta Crop Protection AG, Basel (CH)

( * ) Notice: Subject to any disclaimer, the term of this patent is extended or adjusted under 35 U.S.C. 154(b) by 44 days.

(21) Appl. No.: 12/658,208

(22) Filed: Feb. 4, 2010

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell
(74) *Attorney, Agent, or Firm* — S. Matthew Edwards

(57) ABSTRACT

A new Poinsettia plant named 'SYEP22432' particularly distinguished by the bright red flower color, relatively large inflorescences with bracts a little upright directed, dark green foliage, early flowering response, and medium to strong vigor with good branching.

2 Drawing Sheets

Figure 1:
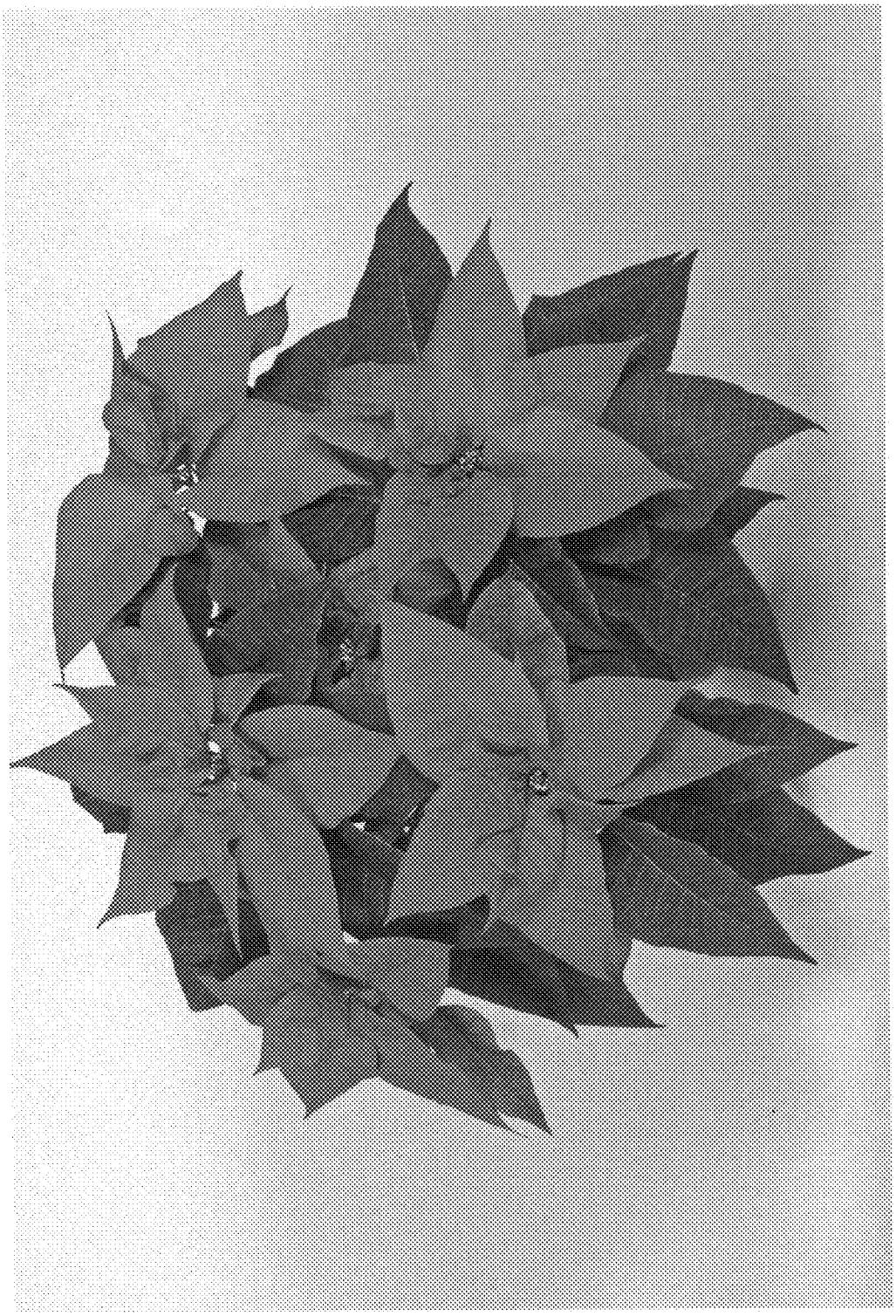

Latin name of the genus and species of the plant claimed: *Euphorbia pulcherrima.*

Varietal denomination: 'SYEP22432'.

BACKGROUND OF THE NEW PLANT

The present invention comprises a new Poinsettia, botanically known as *Euphorbia pulcherrima,* and hereinafter referred to by the variety name 'SYEP22432'.

'SYEP22432' is a product of a planned breeding program. The new cultivar has bright red flower color, relatively large inflorescences with bracts a little upright directed, dark green foliage, early flowering response, and medium to strong vigor with good branching.

'SYEP22432' originated from a hybridization made in the summer of 2003 in a controlled breeding environment in Hillscheid, Germany. The seed was sown in February 2004. The first act of asexual reproduction was accomplished in July 2004, when the shoot tip of each seedling plant was propagated.

The female parent was the proprietary plant designated '# 892', unpatented, with deep bluish red bract color, larger dark green leaves, upright and vigorous habit, and mid-season flowering response.

The male parent of 'SYEP22432' was the proprietary plant designated as 'Fispoin 7776' with large red bracts, dark green foliage with moderate lobes and about medium sized plant habit with relatively upright directed stems.

'SYEP22432' was selected as one flowering plant within the progeny of the stated cross in December 2004 in a controlled environment in Hillscheid, Germany. In April 2005, additional shoot tips were cut and grafted on rootstocks of the variety 'Maren', in order to improve the branching ability. Shoot tip cuttings from the successfully grafted stems were rooted in the summer of 2006 and cultivated for the first trial through the fall and winter of 2006 in a greenhouse in Hillscheid, Germany.

BRIEF SUMMARY OF INVENTION

Horticultural examination of plants grown from cuttings of the plant initiated in April 2005, and continuing thereafter, has demonstrated that the combination of characteristics as herein disclosed for 'SYEP22432' are firmly fixed and are retained through successive generations of asexual reproduction.

'SYEP22432' has not been observed under all possible environmental conditions. The phenotype may vary significantly with variations in environment such as temperature, light intensity and day length.

Plant Breeder's Rights for this cultivar were applied for in Canada on Feb. 11, 2009 and in Switzerland on Mar. 19, 2009. 'SYEP22432' has not been made publicly available more than one year prior to the filing of this application.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawing shows typical flower and foliage characteristics of 'SYEP22432' with colors being as true as possible with an illustration of this type. The photographic drawings show flowering potted plants of the new variety.

Figure 2:
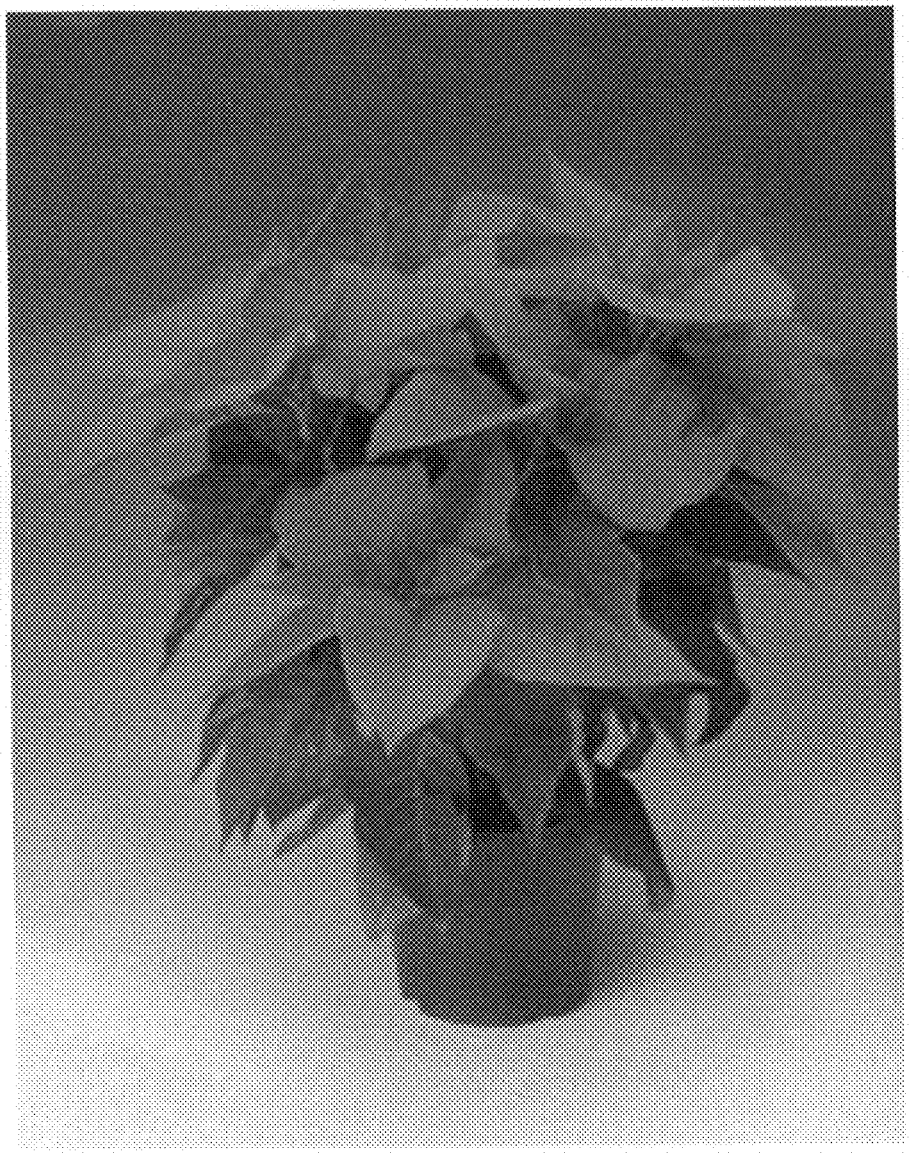

FIG. 1, taken on Nov. 12, 2008 shows a view of the bracts from the top of plant, on a plant about 20 weeks old;

FIG. 2, taken on Nov. 20, 2008, shows a side view of a 16 week old plant.

DETAILED BOTANICAL DESCRIPTION

The measurements were taken in Hillscheid, Germany in mid December 2008 on about 20 week old plants growing in a greenhouse. Culture of these plants had started in late July 2008 with planting rooted cuttings in 14 cm pots and terminal pinching about 2 weeks later. The plants were grown under natural day light in the fall (no black cloth to initiate earlier flowering) and at the moderately warm temperature of 18° C. for the bench heating.

Color references are made to The Royal Horticultural Society Colour Chart (R.H.S.) 2001.

TABLE 1

DIFFERENCES BETWEEN THE NEW VARIETY 'SYEP22432' AND A SIMILAR VARIETY

| | 'SYEP22432' | 'Fismille' (U.S. Plant Pat. No. 13,660) |
|---|---|---|
| Bract color: | More bluish-red | Bright red |
| Bract direction: | More upright directed | Little less upright directed |
| Bract substance: | Less wrinkled | More wrinkled |
| Petiole length: | Shorter | Longer |
| Flowering response: | Slightly earlier | Slightly later |

Plant:

*Form, growth and habit.*—Shrub, with the branches slanting upright, good branching.

*Plant height* (*inflorescence included*).—36-36.5 cm.

*Plant width.*—49-50 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 7-9 leaves per branch.

*Immature, leaf color, upper surface.*—Approximately RHS 143A.

*Lower surface.*—RHS 144B.

*Mature, leaf color, upper surface.*—RHS 139A.

*Lower surface.*—RHS 137D.

*Length.*—13-14 cm.

*Width.*—9-10 cm.

*Shape.*—Ovate, with almost no lobes.

*Base shape.*—Truncate to obtuse.

*Apex shape.*—Acuminate.

*Margin.*—Entire; lobes, when present mostly rounded.

*Aspect.*—Leaf blades are horizontally or slightly downwards directed.

*Texture, upper surface.*—Smooth.

*Lower surface.*—Smooth, apart from the protruding veins.

*Color of veins, upper surface.*—RHS 53B or RHS 47A at the base, fading towards the leaf tip.

*Color of veins, lower surface.*—RHS 48A fading towards the leaf tip.

*Petiole color, upper surface.*—RHS 60A.

*Lower surface.*—RHS 53B.

*Length.*—Most often 7-8 cm.

*Diameter.*—0.2-0.3 cm.

*Aspect.*—Horizontally to slightly upward directed.

*Texture.*—Glabrous.

Stem:

*Quantity of main branches per plant.*—About 7-8.

*Color of stem.*—Mainly RHS 146A to RHS 146B; RHS 176B and RHS 182A at the upper third of the stems.

*Length of stem.*—28-33 cm.

*Diameter.*—0.6-0.8 cm.

*Length of internodes.*—2.5-4.5 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically* (*opening of the stamina, shedding of pollen*).—Late November.

*Flowering, commercially* (*sufficiently colored bracts*).—Mid November.

*Flowering response time.*—About 7-7.5 weeks from equinox.

*Duration of flowering.*—Depends on light and environment, at least 4-6 weeks of 'shelf' life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—25-27 cm.

*Inflorescence, vertical diameter.*—3.5-4.5 cm.

*Number of completely colored bracts per inflorescence* (*sized over 2 cm*).—12-14.

*Single bract, shape.*—Ovate with relatively long, pointed tips, without or with weak lobes.

*Bract, apex.*—Acuminate.

*Bract, base.*—Weakly rounded.

*Single bract, length of blade.*—13 cm, younger bracts diminishing in size.

*Single bract, width of blade.*—8.8 cm.

*Bract color, upper side.*—Between RHS 46B and RHS 46C.

*Bract color, lower side.*—Slightly more bluish than RHS 46D.

*Vein color, upper surface.*—Indistinct, similar as bract blade.

*Vein color, lower surface.*—Approximately RHS 48B.

*Texture.*—Weakly rugose, glabrous.

*Bract petiole color, upper surface.*—RHS 53B.

*Bract petiole color, lower surface.*—Approximately RHS 47A, occasionally as light pink as RHS 51C.

*Bract petiole, length.*—About 2.0 cm, shorter with younger bracts.

*Bract petiole diameter.*—0.2-0.3 cm.

*Cyme* (*true inflorescence*) cyme, diameter.—1.7-2.0 cm.

*Number of cyathia.*—5-10, borne in a tight cluster.

*Cyathium, shape.*—Ovate.

*Cyathium, diameter.*—0.4-0.5 cm.

*Cyathium, length.*—0.6-0.7 cm.

*Color.*—RHS 144A to RHS 144B, top is RHS 46B.

*Nectar cups.*—Usually one per cyathium.

*Nectur cup, width.*—0.4-0.5 cm.

*Nectar cup, color.*—RHS 17A to RHS 32A, a little reddish infusion may occur at the margin: RHS 33A to 33B, or 40B.

Reproductive organs:

*Stamen* (*actually reduced male florets*).—Usually in a small bunch of 10-20 at the top of the cyathium.

*Shape.*—Strap-like.

*Filament length.*—0.2 cm.

*Filament color.*—RHS 46A to RHS 46B.

*Anther color.*—RHS 11A.

*Anther diameter.*—0.1 cm.

*Pollen quantity.*—Moderate (normal quantity).

*Pollen color.*—RHS 12A.

*Female flowers.*—Appear sparse in mid winter, as occurrence depends much on light intensity, appear (if at all) about 4 weeks later than the stamen, a single flower emerges from the top of the cyathium with a short pedicel.

*Style, length.*—0.2-0.3 cm.

*Stigma shape.*—Trifurcate, 6-lobed.

*Style and stigma color.*—RHS 46A to RHS 46B.

*Ovary shape.*—Obovate, 3 ovules.

*Ovary size.*—0.3-0.4 cm in diameter (probably larger in seasons or regions with higher light intensity).

*Ovary color.*—RHS 143A.

*Fertility/seed set.*—Has not been observed on this plant.

Disease/pest resistance: Disease/pest resistance has not been observed on this plant.

What is claimed is:

1. A new and distinct variety of Poinsettia plant named 'SYEP22432,' substantially as illustrated and described herein.

* * * * *